United States Patent [19]
Heller

[11] Patent Number: 5,173,803
[45] Date of Patent: Dec. 22, 1992

[54] PIVOTING DEVICE FOR SUPPORTING FRAMES FOR OPTICAL OBSERVATION EQUIPMENT

[75] Inventor: Rudolf Heller, Zurich, Switzerland

[73] Assignee: Carl-Zeiss-Stiftung, Heidenheim, Fed. Rep. of Germany

[21] Appl. No.: 760,597

[22] Filed: Sep. 16, 1991

[30] Foreign Application Priority Data

Sep. 19, 1990 [DE] Fed. Rep. of Germany ....... 4029638

[51] Int. Cl.⁵ .......................... G02B 7/24; G02B 23/16
[52] U.S. Cl. ..................................... 359/384; 359/391; 359/392; 359/393
[58] Field of Search ............... 359/861, 862, 384, 391, 359/392, 393, 394

[56] References Cited

U.S. PATENT DOCUMENTS

| | | | |
|---|---|---|---|
| 3,640,600 | 2/1972 | Isobe | 359/384 X |
| 4,290,666 | 9/1981 | Rüdel | 359/384 X |
| 4,362,355 | 12/1982 | Takahashi | 359/393 X |
| 4,815,832 | 3/1989 | Hagano et al. | 359/384 |

FOREIGN PATENT DOCUMENTS 0293228 11/1988 European Pat. Off. .
3147836 7/1982 Fed. Rep. of Germany .
81/03054 10/1981 PCT Int'l Appl. .
482439 1/1970 Switzerland .

*Primary Examiner*—Eugene R. LaRoche
*Assistant Examiner*—Do Hyun Yoo
*Attorney, Agent, or Firm*—Eugene Stephens & Associates

[57] ABSTRACT

The disclosed pivoting device is used with a frame structure that supports optical units, such as surgical microscopes and the like, for viewing a predetermined observation point, the frame structure being adjustable in height and in relation to three coordinate axes. The pivoting device carries the optical unit and permits adjustment of the unit about three axes of rotation to any desired position over a spherical surface. The pivoting device includes counterbalancing apparatus that adjusts synchronously with the movement of the optical unit. With this apparatus, it is easy to move the optical unit, and minor adjustments in the position of the optical unit do not require an adjustment of the frame structure. In addition, since the pivoting device's three primary axes of rotation all intersect at the observation point, focus of the optical unit relative to the observation point is not changed by such minor spatial adjustments of the unit.

7 Claims, 3 Drawing Sheets 5,173,803

PIVOTING DEVICE FOR SUPPORTING FRAMES FOR OPTICAL OBSERVATION EQUIPMENT

TECHNICAL FIELD

The invention relates to a spatially-adjustable supporting frame for a surgical microscope which can be locked in any position.

BACKGROUND

Swiss Patent No. 482 439 discloses a surgical microscope support that consists of a coupled-hinge parallelogram frame which is adjustable on three coordinate axes, in combination with a pivoting device that can be pivoted about two axes of rotation.

However, this prior art support frame is bulky in its dimensions, and it is too unwieldy for those uses where the optical observation unit needs to be adjusted only as to height and in translation along the pivoting device's two coordinate axes. Furthermore, the limited pivotability of surgical microscopes held by this prior art device (i.e., about only two axes of rotation) does not meet all the surgeon's requirements, e.g., in the case of difficult brain surgery.

The invention herein is a pivoting device which is itself pivotable about three axes of rotation and which can be combined with known frame structures that can be adjusted on three coordinate axes to provide a support for optical observation equipment suitable for many applications.

SUMMARY OF THE INVENTION

The pivoting device of the present invention comprises a supporting bar connected with an adjustable, counterbalanced, hinged-parallelogram supporting frame of the type disclosed in my copending U.S. patent application, entitled COUNTERBALANCED SUPPORTING FRAME FOR A SURGICAL MICROSCOPE, and filed on even date herewith. The supporting bar is joined to the frame via a pivot bearing and can be rotated about a first axis of rotation. In addition, the supporting bar is inclined relative to said first axis of rotation and is connected at one of its ends via a pivot bearing with a swivel arm which can be rotated about a second axis of rotation. The swivel arm is also connected via another pivot bearing with the optical unit, the latter being rotatable about a third axis of rotation. All three axes of rotation intersect at the observation point. The other end of the supporting bar is connected via still another pivot bearing with a balance arm which carries a counterweight. The balance arm can be rotated about a fourth axis of rotation which extends in a vertical direction relative to its longitudinal axis.

In the preferred embodiment of the invention disclosed herein, the angle subtended by the second and the third axes of rotation is at least 30°, and the fourth axis of rotation of the balance arm is parallel to the second axis of rotation of the swivel arm.

The swivel arm is connected with the balance arm by a drive means that facilitates positioning of the optical unit. The drive means synchronizes the rotation of the balance arm with the rotation of the swivel arm and may comprise any conventional apparatus appropriate for this purpose, e.g., sprocket wheels mounted, respectively, on each pivot bearing and connected by means of a belt or a chain; or a conventional bevel-gear drive; etc.

DRAWINGS

DETAILED DESCRIPTION OF PREFERRED EMBODIMENTS

Figure 1:
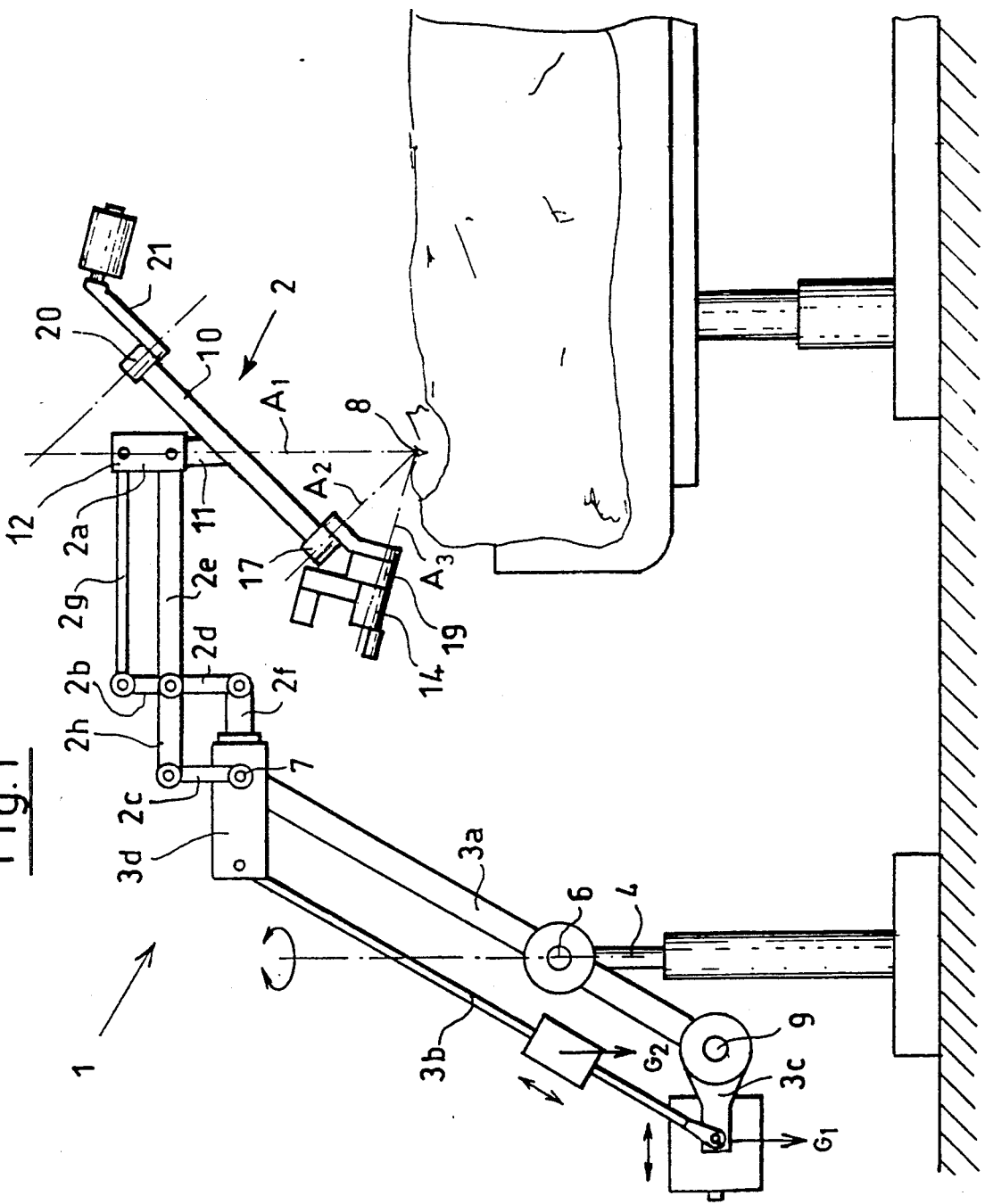
FIG. 1 shows a supporting frame comprising the combination of a pivoting device according to the invention with an adjustable structure which can be adjusted for height and in relation to three spatial coordinates.

FIG. 1 shows an adjustable supporting frame 1 (as disclosed in my above-identified copending application) which can be adjusted in three coordinate directions, in combination with the inventive pivoting device 2. Adjustable frame 1 consists of a vertical column support 4 that is connected with a hinged parallelogram $3a,3b,3c,3d$ via a pivot bearing 6. One side of hinged parallelogram $3a,3b,3c,3d$ is configured as a two-armed lever $3a$ and is rotatable in pivot bearing 6. The side opposite lever $3a$ is a bar $3b$ along which a weight G2 can be moved in an axial direction. Another movable counterweight G1 is cantilevered from a hinge connection 9 so that it is adjustable as indicated by the arrows along a path parallel to the side $3c$ of the parallelogram. A hinge connection 7 between lever $3a$ and adjacent side $3d$ of the parallelogram is connected with another coupled-hinge parallelogram $2a–2h$ which supports the pivoting device 2 via another pivot bearing 12.

Figure 2:
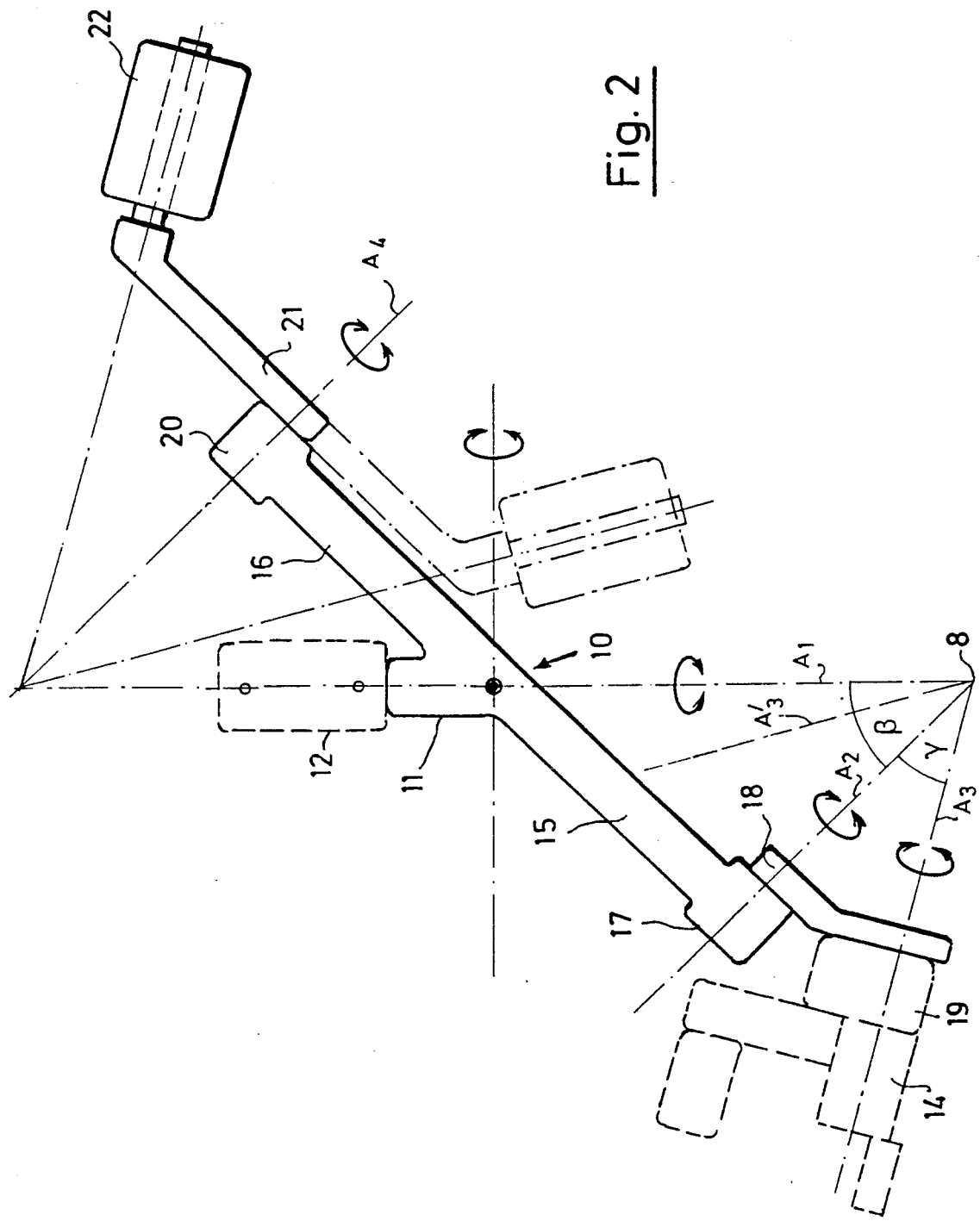
FIG. 2 is an enlarged schematic view of the inventive pivoting device, the optical observation unit being indicated in broken lines.

As can best be seen in the enlarged view of FIG. 2, pivoting device 2 comprises a two-armed supporting bar 10 that is rotatable about its first geometric axis Al in that it has a projecting bearing shaft 11 which is held in pivot bearing 12 mounted to the coupled-hinge parallelogram portion of supporting frame 1. Bar 10 has a first arm 15 that extends in a downward inclined manner from the region where it is connected with supporting frame 1, pointing toward the operator's surgical microscope or other observation unit 14. With this arrangement, observation unit 14 may be positioned well below support 1 and a large adjustment range is created within which the operator is confined as little as possible by the structural elements of the supporting frame.

The angle of inclination of observation unit 14 can be adjusted relative to the horizontal plane for observing in all directions around axis $A_1$ without necessitating a change of focus. This desirable result is achieved by the following structure: A swivel arm 18, which is supported by a pivot bearing 17 on one end of arm 15, in turn supports observation unit 14 by means of a pivot bearing 19. The respective axes of rotation $A_1,A_2,A_3$ (of supporting bar 10, swivel arm 18, and observation unit 14) all intersect at the observation point 8. The axes of rotation $A_2,A_3$ subtend an angle $\gamma$ which, preferably, is no larger than the angle $\beta$ that subtends the axes of rotation $A_1,A_2$ so that the axis of rotation $A_3$ of observation unit 14 can be pivoted in an upward direction until it is nearly in coincidence with the axis of rotation $A_1$ of bar 10. Such an upward position is indicated in broken lines and identified as axis $A'_3$.

Observation unit 14 can be moved easily about the primary axes of rotation $A_1,A_2,A_3$, since the unit's movement is synchronously balanced in that its supporting swivel arm 18 is connected by a drive with a balance arm 21 held by a pivot bearing 20 on the other arm 16 of two-armed supporting bar 10. At its extreme end, balance arm 21 supports a weight 22 for counterbalancing observation unit 14, the mass of which is determined by the length ratios of balance arm 21, swivel arm 18, and arms 15,16 of supporting bar 10.

The drive connection between swivel arm 18 and balance arm 21 consists of a chain belt 23 which meshes with a pair of sprocket wheels 24,25 which are mounted respectively to the shaft pins 26,27 of the pivot bearings 17,20. Of course, the use of other known drive connections is also conceivable, e.g., a bevel-gear drive.

Figure 3:
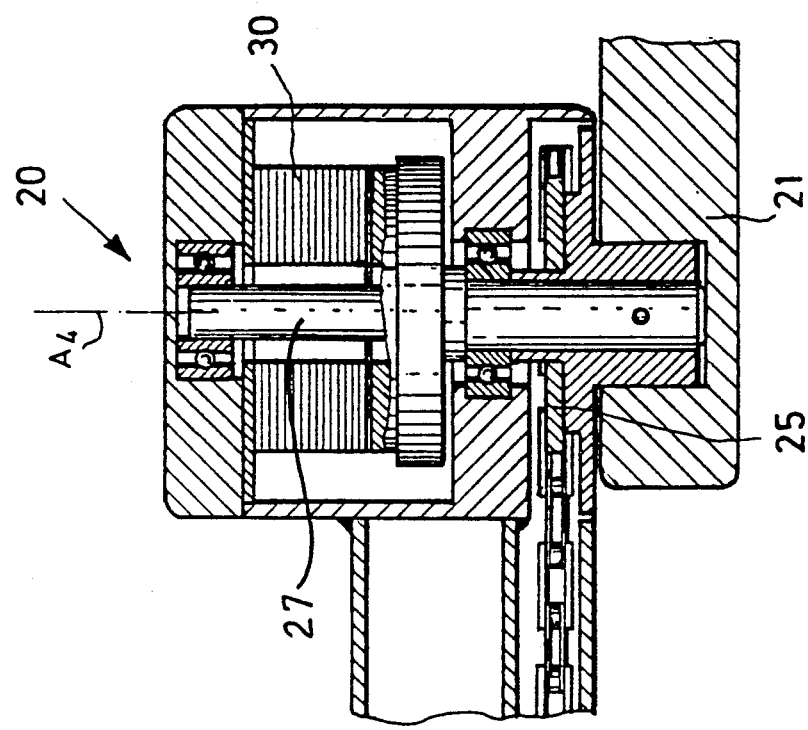
FIG. 3 is a partial sectional and further enlarged view of the supporting bar portion of the pivoting device, showing pivot bearings at its respective ends.
Figure 3:
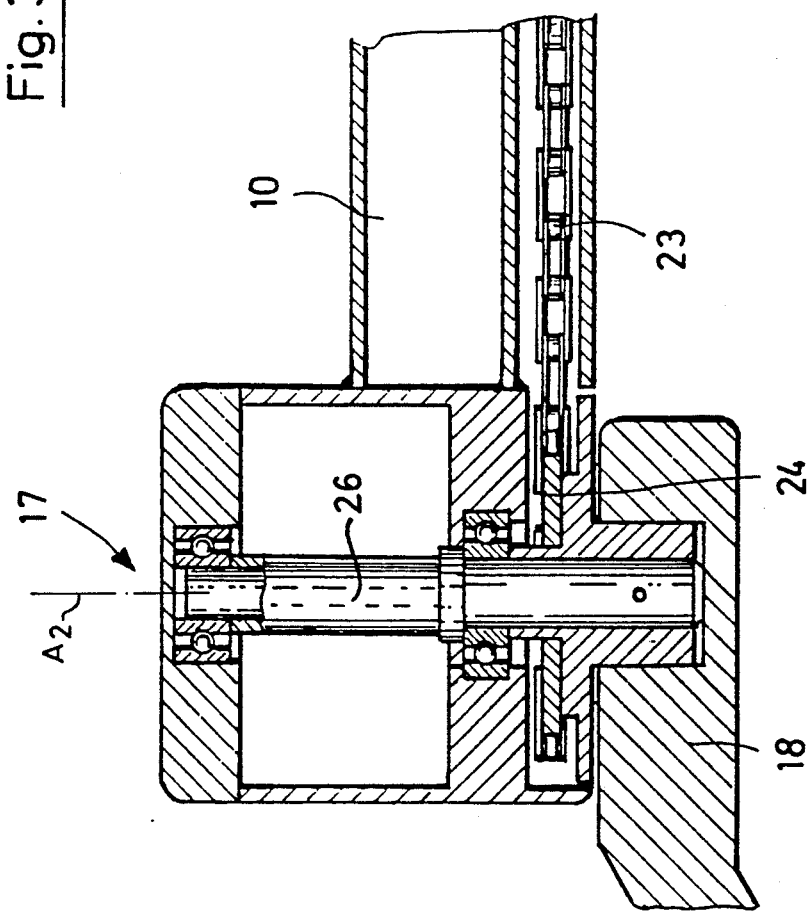

The observer adjusts the position of supporting device 2 during a surgical procedure by appropriate means, e.g., by guiding a mouthpiece connected to observation unit 14. The position of supporting device 2 is then fixed by locking one or more of the pivot bearings 12,17,19,20. In the embodiment shown in FIG. 3, pivot bearing 20 is locked by means of an electromagnetic brake 30 which is activated by appropriate means, e.g., by a foot-pedal control or a hand-grip switch (not shown).

I claim:

1. A pivoting device for a frame structure used to support optical units, such as surgical microscopes, for viewing a predetermined observation point, said frame structure being adjustable in height and in relation to three coordinate axes, said pivoting device comprising:
    a supporting bar rotatably connected to said frame structure for movement about a first axis, said supporting bar being inclined to said first axis and having first and second pivot bearings positioned at its respective ends;
    a swivel arm rotatably connected at one of its ends to the first pivot bearing of said supporting bar for movement about a second axis;
    optical unit holding means, located at the other end of said swivel arm, for holding said optical unit and permitting said unit to rotate about a third axis;
    said first, second, and third axes all intersecting at said observation point; and
    a balance arm carrying a counterweight at one of its ends and having its other end connected to the second pivot bearing of said supporting bar for rotation about a fourth axis which extends perpendicular to the longitudinal axis of said balance arm.

2. The pivoting device of claim 1 wherein the angle subtended by the second and third axes of rotation is at least 30° but no greater than the angle subtended by the first and second axes of rotation.

3. The pivoting device of claim 1 wherein said fourth axis of rotation of said balance arm is parallel to said second axis of rotation of said swivel arm.

4. The pivoting device of claim 1 further comprising drive means interconnecting said swivel arm and said balance arm so that the balance arm is synchronously rotated in response to the rotation of the swivel arm.

5. The pivoting device of claim 4 wherein said drive means between the swivel arm and the balance arm comprises sprocket wheels interconnected by a belt or a chain.

6. The pivoting device of claim 4 wherein said drive means between the swivel arm and the balance arm comprises a bevel gear drive.

7. The pivoting device of claim 1 wherein said supporting bar, said swivel arm, said optical unit holding means, and said balance arm which are rotatable, respectively, about said four axes of rotation are mounted in respective pivot bearings, and further comprising electromagnetic brake means associated with at least one of said pivot bearings for locking said one pivot bearing in an adjusted position.

* * * * *